(12) United States Patent
Vergani et al.

(10) Patent No.: US 6,797,182 B2
(45) Date of Patent: Sep. 28, 2004

(54) PROCESS FOR THE PURIFICATION OF ORGANOMETALLIC COMPOUNDS OR HETEROATOMIC ORGANIC COMPOUNDS WITH HYDROGENATED GETTER ALLOYS

(75) Inventors: Giorgio Vergani, Monza (IT); Marco Succi, Milan (IT)

(73) Assignee: Saes Getters S.p.A., Lainate (IT)

( * ) Notice: Subject to any disclaimer, the term of this patent is extended or adjusted under 35 U.S.C. 154(b) by 112 days.

(21) Appl. No.: 10/273,862

(22) Filed: Oct. 18, 2002

(65) Prior Publication Data

US 2003/0038082 A1 Feb. 27, 2003

Related U.S. Application Data

(63) Continuation of application No. PCT/IT01/00185, filed on Apr. 13, 2001.

(30) Foreign Application Priority Data

Apr. 19, 2000 (IT) .................................... MI2000A0882
Apr. 20, 2000 (IT) .................................... MI2000A0892

(51) Int. Cl.$^7$ .............................................. B01D 53/00
(52) U.S. Cl. .................. 210/757; 210/763; 260/665 R; 423/210; 423/219; 556/1
(58) Field of Search ............................... 423/210, 219, 423/248; 260/665 R; 556/1; 210/757, 758, 763

(56) References Cited

U.S. PATENT DOCUMENTS

| 4,312,669 A | 1/1982 | Boffito et al. |
| 4,457,891 A | 7/1984 | Bernauer et al. |
| 5,180,568 A | 1/1993 | Boffito et al. |
| 5,260,585 A * | 11/1993 | Tom .......................... 250/573 |
| 5,385,689 A * | 1/1995 | Tom et al. .................. 252/194 |
| 5,470,555 A | 11/1995 | Shimada et al. |
| 5,531,971 A * | 7/1996 | Tom et al. .................. 423/210 |
| 5,716,588 A | 2/1998 | Vergani et al. |
| 5,961,750 A | 10/1999 | Boffito et al. |
| 6,521,192 B1 * | 2/2003 | Weber et al. ................ 422/177 |

FOREIGN PATENT DOCUMENTS

| EP | 0 444 422 A1 | 9/1991 |
| EP | 0 470 936 B1 | 12/1994 |
| EP | 0 869 195 A1 | 10/1998 |
| EP | 0 960 647 A1 | 12/1999 |

* cited by examiner

Primary Examiner—Ernest G. Therkorn
(74) Attorney, Agent, or Firm—Akin Gump Strauss Hauer & Feld, LLP

(57) ABSTRACT

A process for the purification of organometallic compounds or heteroatomic organic compounds from oxygen, water and from the compounds deriving from the reaction of water and oxygen with the organometallic or heteroatomic compounds whose purification is sought, comprising the operation of contacting the organometallic or heteroatomic compound to be purified in the liquid state or in form of vapor, pure or in a carrier gas, with a hydrogenated getter alloy, and optionally also with one or more gas sorber materials selected among palladium on porous supports and a mixture of iron and manganese supported on zeolites.

22 Claims, 2 Drawing Sheets

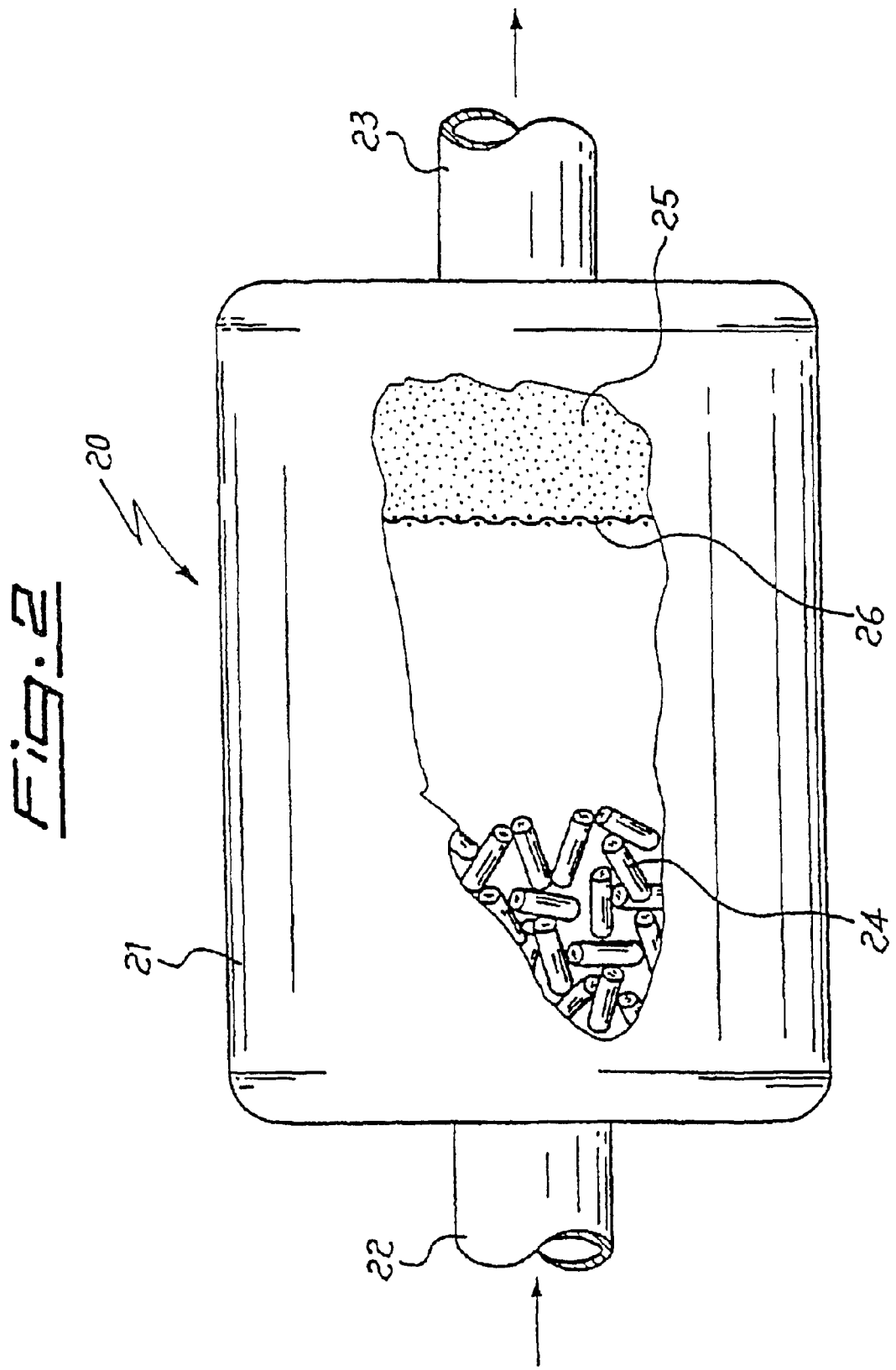

PROCESS FOR THE PURIFICATION OF ORGANOMETALLIC COMPOUNDS OR HETEROATOMIC ORGANIC COMPOUNDS WITH HYDROGENATED GETTER ALLOYS

CROSS-REFERENCE TO RELATED APPLICATIONS

This application is a continuation of International Application No. PCT/IT01/00185, filed Apr. 13, 2001, which was published in the English language on Oct. 25, 2001 as International Publication No. WO 01/079587 A1 and the disclosure of which is incorporated herein by reference.

BACKGROUND OF THE INVENTION

The present invention relates to a process for the purification of organometallic compounds or heteroatomic organic compounds with hydrogenated getter alloys.

Organometallic compounds are characterized by the presence of a bond between one metal atom (also arsenic, selenium or tellurium being included among metals) and one carbon atom being part of an organic radical such as, for example, aliphatic or aromatic, saturated or unsaturated hydrocarbon radicals; by extension, with the definition of organometallic compounds also the compounds including metal atoms bound to organic radicals by means of an atom other than carbon, such as for instance the alcoholic radicals (—OR) or of esters (—O—CO—R) are meant.

The heteroatomic organic compounds (also simply defined heteroatomic in the following) are those organic compounds comprising, further to carbon and hydrogen, also atoms such as oxygen, nitrogen, halides, sulfur, phosphorus, silicon and boron.

Many of these compounds have been used for a long time in traditional chemical applications. Reagents having very high purity are not generally requested in this field, and their purification is carried out by techniques such as distillation (optionally at reduced pressure, in order to reduce the boiling temperature and therefore the risks of thermal decomposition of the compounds) or re-crystallization from solvents.

However, these compounds have been recently used in high technology applications, particularly in the semiconductor industry. In these applications, the organometallic compounds and the heteroatomic compounds are used as reagents in the processes of chemical deposition from the gaseous state (known in the field with the definition "Chemical Vapor Deposition" or with the acronym CVD). In these techniques, a gas flow of one or more organometallic or heteroatomic compounds (or a flow of a carrier gas containing a known concentration thereof) is conveyed into a process chamber; then, inside the chamber the compounds are decomposed or reacted, so that materials containing metal atoms or heteroatoms are formed in situ (generally in the form of thin layers). The organometallic or heteroatomic compounds can be already in the gaseous form, but they can also be in the liquid form. In this second case, the gaseous flow of the compound is obtained either by evaporating the compound, in which case the flow is composed only of the compound of interest, or by bubbling a gas in the container for the liquid, in which case the flow contains vapors of the compound in the carrier gas.

The main organometallic gases used in these applications are hafnium tetra-t-butoxide, trimethylaluminum, triethylaluminum, tri-t-butylaluminum, di-i-butylaluminum hydride, dimethylaluminum chloride, diethylaluminum ethoxide, dimethylaluminum hydride, trimethylantimony, triethylantimony, tri-i-propylantimony, tris-dimethylaminoantimony, phenylarsine, trimethylarsenic, tris-dimethylamino-arsenic, t-butylarsine, barium bis-tetrameitylyheptanedionate, bismuth tris-tetramethylheptanedionate, dimethylcadmium, diethylcadmium, iron pentacarbonyl, iron bis-cyclopentadienyl, iron tris-acetylacetonate, iron tris-tetramethylheptanedionate, trimethylgallium, triethylgallium, tri-i-propylgallium, tri-i-butylgallium, trimethylindium, triethylindium, ethyldimethylindium, yttrium tris-tetramethylheptanedionate, lanthanum tris-tetramethylheptanedionate, magnesium bis-methylcyclopentadienyl, magnesium bis-cyclopentadienyl, magnesium bis-tetramethylheptanedionate, dimethylmercury, dimethylgold acetylacetonate, lead bis-tetramethylheptanedionate, bis-hexafluorocopper acetylacetonate, copper bis-tetramethylheptanedionate, dimethylselenium, diethylselenium, scandium tris-tetramethylheptanedionate, tetramethyltin, tetraethyltin, strontium bis-tetramethylheptanedionate, tantalum tetraethoxy-tetramethylheptanedionate, tantalum tetramethoxytetramethylheptanedionate, tantalum tetra-i-propoxytetramethylheptanedionate, tantalum tri-diethylamido-t-butylimide, diethyltellurium, di-i-propyltellurium, dimethyltellurium, titanium bis-i-propoxy-bis-tetramethylheptanedionate, titanium tetradimethylamide, titanium tetradiethylamide, dimethylzinc, diethylzinc, zinc bis-tetramethylheptanedioniate, zirconium tetra-tetramethylheptanedionate, zirconium tri-i-propoxy-tetramethylheptanedionate and zinc bis-acetylacetonate.

The principal heteroatomic compounds used in these applications are trimethylborane, asymmetric dimethylhydrazine (that is, wherein both methyl groups are bound to the same nitrogen atom), t-butylamine, phenylhydrazine, trimethylphosphorus, t-butylfosfine and t-butylmercaptane.

Some typical examples of application of these methods are the production of the semiconductors of type III-V, such as GaAs or InP, or of type II-VI such as ZnSe; the use for p doping (for instance with boron) or n doping (for instance with phosphorus) of traditional silicon-based semiconductors; the production of materials having a high dielectric constant (for example compounds such as $PbZr_xTi_{1-x}O_3$) used in ferroelectric memories; or the production of materials having a low dielectric constant (such as $SiO_2$) for isolating electric contacts in semiconductor devices.

For these applications reagents having an extremely high purity are required, with levels of the order of $10^{-1}$–$10^{-2}$ ppm, whereas the traditional chemical techniques do not allow to obtain levels of impurities lower than about ten ppm. Further, even in the case that organometallic or heteroatomic compounds having high purity are produced, the storage is source of contamination due to gas release from the container walls, which anyway makes necessary to use a purifier immediately before the application (so-called "point-of-use" purifiers).

U.S. Pat. No. 5,470,555 describes the removal from organometallic compounds of oxygen gas which is present as an impurity, by using of a catalyst formed of copper or nickel metals, or the relevant oxides activated by reduction with hydrogen, deposited on a support such as alumina, silica or silicates. According to the patent, by this method the removal of oxygen gas from a flow of the organometallic compound can be obtained, to values of $10^{-2}$ ppm.

However, oxygen is not the only impurity that has to be removed from the organometallic or heteroatomic compounds. Other harmful impurities in the CVD processes are for example water and, particularly, the species deriving from the alteration of the same organometallic or heteroatomic compound, following to undesired reactions generally with water or oxygen. For instance, in the case of a generic organometallic compound $MR_n$, wherein M represents the metal, R an organic radical and n the valence of the metal M, contamination from $MR_{n-x}$ $(-OR)_x$ species can occur, wherein x is an integer varying between 1 and n. These oxygenated species are harmful in the CVD processes because they introduce oxygen atoms into the material being formed, thus sensibly altering the electric properties thereof.

BRIEF SUMMARY IF THE INVENTION

Object of the present invention is providing a process for the purification of organometallic compounds or heteroatomic organic compounds from oxygen, water and from the compounds derived from the reaction of water and oxygen with organometallic or heteroatomic compounds whose purification is sought.

This object is obtained according to the present invention with a process wherein the organometallic or heteroatomic compound to be purified is contacted with a hydrogenated getter alloy. The purification can be carried out on the organometallic or heteroatomic compound both in the liquid and in the vapor state.

It is also possible to use, in addition to the getter alloy, other impurity sorbing materials, such as palladium on porous supports or a mixture of iron and manganese supported on zeolites.

The use of getter alloys for the purification of noble gases, nitrogen or hydrogen to be used in the microelectronic industry is known. Further, it is known from patent EP-B-470936 the use of hydrogenated getter alloys for the purification of simple hydrides, such as $SiH_4$, $PH_3$ and $AsH_3$.

However, it has been found that a hydrogenated getter alloy is also capable of removing water and oxygen from an organometallic or heteroatomic compound (liquid or as a vapor, pure or in a carrier gas), and of converting the species containing oxygen of the type $MR_{n-x}(-OR)_x$ to the original compound or to compounds of the type $MR_{n-x}H_x$ which are not harmful to the CVD processes because they do not contain oxygen.

BRIEF DESCRIPTION OF THE SEVERAL VIEWS OF THE DRAWINGS

The foregoing summary, as well as the following detailed description of preferred embodiments of the invention, will be better understood when read in conjunction with the appended drawings. For the purpose of illustrating the invention, there is shown in the drawings embodiments which are presently preferred. It should be understood, however, that the invention is not limited to the precise arrangements and instrumentalities shown.

In the drawings:

FIG. 2 shows a cutaway view of a purifier by which it is possible to put into practice a second embodiment of the process according to the invention.

DETAILED DESCRIPTION OF THE INVENTION

Figure 1:
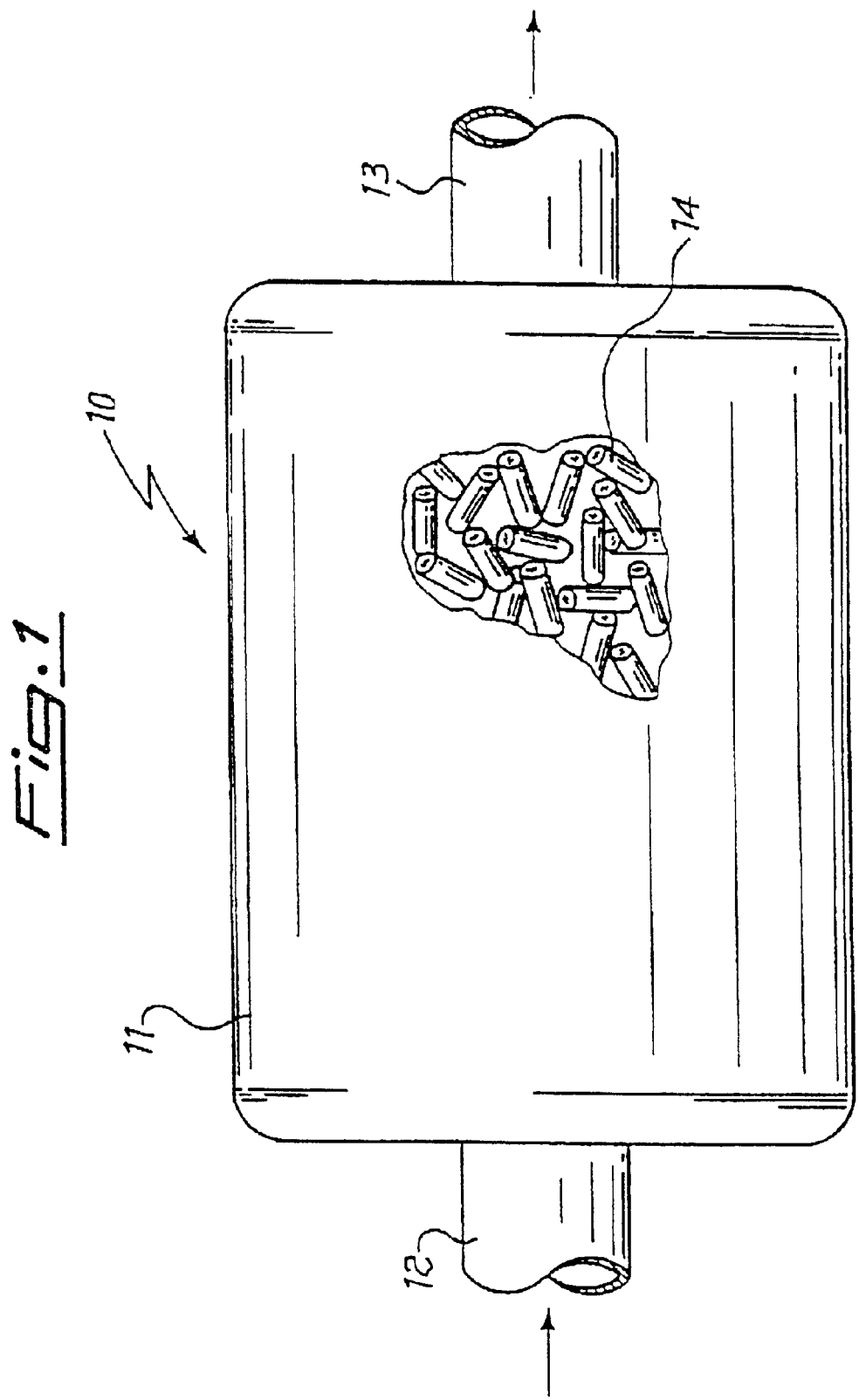
FIG. 1 shows a cutaway view of a purifier by which it is possible to put into practice a first embodiment of the process according to the invention.

In one embodiment thereof, the process of the invention consists in contacting the hydrogenated getter alloy with the compound to be purified in the liquid state. This can be carried out simply by introducing the getter alloy into the container of the liquid compound, from which the same will be evaporated by heating or with a carrier gas.

However, in a preferred embodiment the purification is carried out by contacting the hydrogenated getter alloy with vapors, pure or in a carrier gas, of the organometallic or heteroatomic compound. In the following, the invention will be described with particular reference to the purification in the vapor state, since this is the condition most commonly used in the industry.

The getter alloys suitable for the invention are the alloys based on titanium and/or zirconium with one or more elements chosen amongst transition metals and aluminum, and mixtures of one or more of these alloys and titanium and/or zirconium. In particular, useful for the invention are:

the $ZrM_2$ alloys, wherein M is one or more among Cr, Mn, Fe, Co or Ni transition metals, as described in U.S. Pat. No. 5,180,568 in the Applicant's name;

intermetallic compound $Zr_1Mn_1Fe_1$, produced and sold by Applicant under the name St 909;

the Zr-V-Fe alloys, as described in patent U.S. Pat. No. 4,312,669 in the Applicant's name, whose weight percent composition plotted in a composition ternary diagram is included in a triangle having its vertices in the following points:

a) Zr 75%-V 20%-Fe 5%;

b) Zr 45%-V 20%-Fe 35%;

c) Zr 45%-V 50%-Fe 5%, and particularly the alloy having weight percent composition Zr 70%-V 24.6%-Fe 5.4%, produced and sold by the Applicant under the name St 707;

the intermetallic compound $Zr_1V_1Fe_1$, produced and sold by the Applicant under the name St 737;

the Zr—Co—A alloys as described in U.S. Pat. No. 5,961,750 in the Applicant's name, whose weight percent composition plotted in a composition ternary diagram is comprised in a polygon having its vertices in the following points:

a) Zr 81%-Co 9%-A 10% b) Zr 68%-Co 22%-A 10% c) Zr 74%-Co 24%-A 2% d) Zr 88%-Co 10%-A 2% wherein A means any element selected among yttrium, lanthanum, rare earths or mixtures of these elements, and particularly the alloy having weight percent composition Zr 80.8% -Co 14.2% -A 5%, produced and sold by the Applicant under the name St 787;

the Ti—Ni alloys;

the Ti—V—Mn alloys described in U.S. Pat. No. 4,457,891.

The loading of the above listed alloys with hydrogen is generally carried out with the alloys already in the final container (the body of the purifier). This operation can be carried out at temperatures between room temperature and about 400° C. Temperatures higher than 400° C. are not advisable since the maximum quantity of hydrogen which can be loaded in the alloy decreases with increasing temperature. It is possible to operate with hydrogen pressures up to about 10 bars, and preferably above the atmospheric pressure. Pressures higher than about 10 bars are not advisable since, without offering particular advantages with respect to lower pressures, require the use of special equipment and safety systems, whereas pressures lower than the atmospheric require the use of vacuum systems downstream of the purifier in order to establish the gas flow necessary for the hydrogenation. In practice, the hydrogenation can be carried out in various ways. For example, it is possible to convey a flow of a mixture of hydrogen in another gas (for instance a 50% mixture of hydrogen-argon) on the alloy and to monitor the composition of the output gas, stopping the procedure when in the latter a hydrogen pressure higher than a prefixed value is detected. Alternatively, a defined procedure can be experimentally determined for each alloy. For example, in the case of the above mentioned alloy St 707, an argon flow is conveyed in order to eliminate the air trapped in the system; after few minutes preheating is started at 350° C. under a flow of argon, and hydrogen is introduced with a flow equal to that of argon, so that a 50% mixture of the two gases is formed, maintaining this condition for 3 hours; the argon flow is interrupted, in the meantime reducing the temperature to 150° C. and maintaining this condition for one hour and a half, then, the hydrogen flow is interrupted while the argon flow is re-opened for half of an hour, without heating; at the end, the purifier is isolated by closing two valves positioned upstream and downstream thereof.

The useful temperature range for the purification of organometallic or heteroatomic gases is comprised between room temperature and about 100° C.; at temperatures lower than room temperature, the oxygen removal is limited, whereas at temperatures higher than about 100° C. decomposition reactions of the compound to be purified could take place.

The flow of the gas to be purified can vary between about 0.1 and 20 slpm (liters of gases, measured in standard conditions, per minute) at absolute pressures preferably comprised between about 1 and 10 bars.

This flow can be formed only of the vapors of the compound to be purified, or of said vapors in a flow of carrier gas. The carrier gas can be any gas interfering neither with the hydrogenated getter alloy (or with the other possibly used gas sorbing materials) nor with the deposition process wherein the organometallic or heteroatomic compound is used. Argon, nitrogen or even hydrogen are commonly used.

FIG. 1 shows a cutaway view of a possible purifier to be used in the first embodiment of the process according to the invention. The purifier 10 is formed of a body 11, generally cylindrical; at the two ends of body 11 are present a piping 12 for the inlet of the gas in the purifier, and a piping 13 for the gas outlet. The getter alloy 14 is contained inside body 11. The inlet 12 and the outlet 13 of the gas are preferably provided with standard connections of the VCR type, known in the field (not shown in the figure) for connection with the gas lines upstream and downstream of the purifier. The purifier body can be made with various metal materials; the preferred material for this purpose is steel AISI 316. The internal surfaces of the purifier body, which are in contact with the gas, are preferably electropolished until a surface roughness lower than about 0.5 $\mu$m is obtained. In order to prevent traces of the getter alloy powder from being carried downstream of the purifier by the outlet gas flow, inside the purifier body at outlet 13 can be arranged means for retaining the particulate, such as nets or porous septa generally metallic having size of the "gaps" or of the pores suitable for retaining particles without causing an excessive pressure drop in the gas flow; the size of these openings can generally vary between about 10 and 0.003 $\mu$m. Inside the purifier, the getter alloy 14 can be present in the powder form, but preferably it is used in the form of pellets obtained by compression of the powders as shown in the figure.

The gas flow to be purified can be contacted, further than with the hydrogenated getter alloy, with at least one additional material, selected among palladium on porous supports or a mixture of iron and manganese supported on zeolites, or both.

The material formed of palladium on porous supports contains preferably 0.3–4% by weight of metal. The porous support may be any material normally used for this application, such as, e.g., molecular sieves, zeolites, ceramics or porous glass. Catalysts comprising palladium on porous supports are sold by many companies that manufacture catalysts for the chemical industry, such as the companies Süd Chemie, Degussa and Engelhard. The optimal temperature range for using these materials is comprised between about −20 and 100° C., and preferably between room temperature and 50° C.

The material formed of the mixture of iron and manganese on zeolites has preferably a weight ratio between iron and manganese comprised between 7:1 and 1:1; even more preferably this ratio is about 2:1. This material can be produced according to the modalities described in U.S. Pat. No. 5,716,588 in the Applicant's name. The optimal temperature range for using this material is comprised between about −20 and 100° C., and preferably between room temperature and 50° C.

The additional material (or the additional materials) can be positioned indifferently upstream or downstream of the hydrogenated getter alloy along the direction of the gas flow. It is also possible, when both the cited additional materials are used, that one of them is upstream ad the other one downstream of the hydrogenated getter alloy.

The additional material (or the additional materials) can be provided in a separate body, connected to body 11 of the purifier containing the hydrogenated getter alloy by means of pipings and fittings, for instance of the above mentioned VCR type. Also this second body will be preferably made of the materials and with the finishing level of the surfaces described for body 11.

Preferably, the additional material (or the additional materials) are arranged in the same purifier body wherein the hydrogenated getter alloy is provided. In this case, the different materials can be mixed, but preferably they are separated in the purifier body.

FIG. 2 shows a cutaway view of a possible purifier containing more than one material (the case of two materials is exemplified); in particular, the figure shows a purifier made according to the preferred mode wherein the different materials are kept separated inside the purifier body. The purifier 20 is formed of a body 21, a gas inlet 22 and a gas outlet 23; inside body 21 are arranged, on the side of inlet 22 the hydrogenated getter alloy 24, and on the side of the outlet 23 a material 25 selected between palladium on porous supports or a mixture of iron and manganese supported on zeolites; preferably, between the two materials a mechanical member 26 is arranged which is easily permeable to gases, such as a metal net, in order to help maintaining the separation and the original geometrical arrangement of the materials.

In the case that two different materials are present at the same time in the same body (the situation exemplified in FIG. 2), the purifier must be kept at a temperature compatible with the working temperature of all the present materials, and consequently preferably between room temperature and about 50° C.

Finally, it is also possible to add to the various cited materials also a chemical water sorber, for example calcium oxide or boron oxide, this latter prepared according to the teachings of patent application EP-A-960647 in the Applicant's name.

The invention will be further illustrated in the following example. This example does not limit the scope of the invention and is useful for illustrating a possible embodiment intended to teach those skilled in the art how to put the invention into practice and to represent the way that is considered the best for carrying out the invention.

EXAMPLE 1

A purifier of the type shown in FIG. 1 is made. The purifier has a body made of steel AISI 316 and an internal volume of about 50 cm$^3$. In the purifier, 72 g of St 707 are introduced in pellets, which are hydrogenated according to the previously described procedure. The purifier is then connected, by means of VCR connections, upstream to a nitrogen cylinder containing 40 ppm by volume (ppmv) of water and 100 ppmv of oxygen, and downstream to a mass spectrometer of the APIMS type (atmospheric pressure ionization mass spectrometer) mod. TOF 2000 of the company Sensar, that has a sensing threshold of 10-4 ppmv both for water and for oxygen. The test is carried out in nitrogen instead of in a flow of an organometallic compound vapor, because the analyzing instrument used (APIMS) has a reduced sensibility in the vapors of these compounds, such that a test with an organometallic compound would not enable to obtain significant results. The gas to be purified is passed at 5 bars in the purifier maintained at 100° C., with a flow of 0.1 slpm. At the beginning of the test the quantity of water and oxygen in the gas outlet from the purifier is under the analyzer sensibility threshold, indicating the functionality of the getter hydrogenated alloy in the removal of this species. The test is continued until the analyzer senses in the gas output from the purifier a quantity of contaminant of $10^{-3}$ ppmv; this contamination value of the output gas is adopted as indicator of the purifier depletion. From the knowledge of the test data, it is proved that the purifier has a capacity of 6 l/l (liters of the gas measured in standard conditions per liters of the getter alloy) for oxygen, and 4 l/l for water.

It will be appreciated by those skilled in the art that changes could be made to the embodiments described above without departion from the broad inventive concept thereof. It is understood, therefore, that this invention is not limited to the particular embodiments disclosed, but it is intended to modifications within the spirit and scope of the scope of the present invention as defined by the appended claims.

We claim:

1. A process for the purification of organometallic compounds or heteroatomic organic compounds from oxygen, water and from the compounds derived from the reaction of water and oxygen with the compounds whose purification is sought, comprising the operation of contacting the organometallic or heteroatomic organic compound to be purified with a hydrogenated getter alloy.

2. A process according to claim 1 wherein the hydrogenated getter alloy is contacted with the organometallic or heteroatomic organic compound in the form of vapor, pure or in a carrier gas.

3. A process according to claim 2 wherein said operation is carried out at a temperature comprised between room temperature and about 100° C.

4. A process according to claim 2 wherein said operation is carried out with a flow of the gas to be purified between about 0,1 and 20 slpm, at absolute pressures of about 1 to 10 bars.

5. A process according to claim 1 wherein the hydrogenated getter alloy is an alloy based on titanium and/or zirconium with one or more elements selected among transition metals and aluminum, and mixtures among one or more of these alloys with titanium and/or zirconium, and wherein the loading with hydrogen is carried out at a temperature comprised between room temperature and 400° C. and at a hydrogen pressure lower than 10 bars.

6. A process according to claim 5 wherein the loading of the getter alloy is carried out at a hydrogen pressure which is higher than the atmospheric pressure.

7. A process according to claim 5 wherein the hydrogenated getter alloy is an alloy having general formula $ZrM_2$, wherein M is one or more among Cr, Mn, Fe, Co or Ni metals.

8. A process according to claim 5 wherein the hydrogenated getter alloy is an alloy comprising zirconium, vanadium and iron, whose weight percent composition plotted in a ternary diagram of compositions is comprised in a triangle having its vertices in the following points:

a) Zr 75%-V 20%-Fe 5%;
b) Zr 45%-V 20%-Fe 35%;
c) Zr 45%-V 50%-Fe 5%.

9. A process according to claim 5 wherein the hydrogenated getter alloy is an alloy comprising zirconium, cobalt and one or more elements selected among yttrium, lanthanum and rare earths whose weight percent composition plotted in a composition ternary diagram is comprised in a polygon having its vertices in the following points:

a) Zr 81%-Co 9%-A 10%
b) Zr 68%-Co 22%-A 10%
c) Zr 74%-Co 24%-A 2%
d) Zr 88%-Co 10%-A 2% wherein A means any element selected among yttrium, lanthanum, rare earths or mixtures of these elements.

10. A process according to claim 5 wherein the hydrogenated getter alloy is an alloy comprising titanium or nickel.

11. A process according to claim 5 wherein the hydrogenated getter alloy is an alloy comprising titanium, vanadium and manganese.

12. A process according to claim 1 wherein the organometallic compound is selected among hafnium tetra-t-butoxide, trimethylaluminum, triethylaluminum, tri-t-butylaluminum, di-i-butylaluminum hydride, dimethyl aluminum chloride, diethylaluminum ethoxide, dimethylaluminum hydride, trimethylantimony, triethylantimony, tri-i-propylantimony, tris-dimethylamino-antimony, phenylarsine, trimethylarsenic, tris-dimethylamino-arsenic, t-butylarsine, barium bis-tetramethylheptanedionate, bismuth tris-tetramethylheptanedionate, dimethylcadmium, diethylcadmium, iron pentacarbonyl, iron bis-cyclopentadienyl, iron tris-acetylacetonate, iron tris-tetramethylheptanedionate, trimethylgallium, triethylgallium, tri-i-propylgallium, tri-i-butylgallium, trimethylindium, triethylindium, ethyldimethylindium, yttrium tris-tetramethylheptanedionate, lanthanum tris-tetramethylheptanedionate, magnesium bis-methylcyclopentadienyl, magnesium bis-cyclopentadienyl, magnesium bis-tetramethylheptanedionate, dimethylmercury, dimethylgold acetylacetonate, lead bis-tetramethylheptanedionate, bis-hexafluorocopper acetylacetonate, copper bis-tetramethylheptanedionioate, dimethylselenium, diethylselenium, scandium tris-tetramethylheptanedionate, tetraethyltin, tetraethyltin, strontium bis-tetramethylheptanedionate, tantalum tetramethoxytetramethylheptanedionate, tantalum tetramethoxytetramethylheptanedionate, tantalum tetra-i-propoxytetramethylheptanedionate, tantalum tri-diethylamido-t-butylimide, diethyltellurium, di-i- propyltellurium, dimethyltellurium, titanium bis-i-propoxy-bis-tetramethylheptanedionate, titanium tetradimethylamide, titanium tetradiethylamide, dimethylzinc, diethylzinc, zinc bis-tetramethylheptanedionate, zirconium tetra-tetramethylheptanedionate, zirconium tri-i-propoxy-tetramethylheptanedionate and zinc bis-acetylacetonate.

13. A process according to claim 1 further comprising the operation of contacting the organometallic or heteroatomic organic compound to be purified with at least one second material selected among palladium on porous supports and a mixture of iron and manganese supported on zeolites.

14. A process according to claim 13 wherein the second material is a catalyst based on palladium on porous supports with a weight content of 0,3–4% of palladium.

15. A process according to claim 13 wherein the organometallic or heteroatomic compound is in the form of vapor, pure or in a carrier gas.

16. A process according to claim 15 wherein the contact between the compound to be purified and the supported palladium occurs at a temperature comprised between about −20 and 100° C.

17. A process according to claim 15 wherein the contact between the compound to be purified and the supported mixture of iron and manganese occurs at a temperature comprised between about −20 and 100° C.

18. A process according to claim 16 wherein said contact occurs at a temperature comprised between room temperature and 50° C.

19. A process according to claim 13 wherein the second material is a mixture of iron and manganese supported on zeolites, and wherein the weight ratio between iron and manganese is comprised between 7:1 and 1:1.

20. A process according to claim 19 wherein said weight ratio is about 2:1.

21. A process according to claim 17 wherein said contact occurs at a temperature comprised between room temperature and 50° C.

22. A process according to claim 1 further comprising the operation of contacting the organometallic or heteroatomic organic compound to be purified with a chemical water sorber.

* * * * *